US012682625B2

(12) United States Patent
Zhu et al.

(10) Patent No.: US 12,682,625 B2
(45) Date of Patent: Jul. 14, 2026

(54) TRAINING METHOD AND APPARATUS, DIALOGUE PROCESSING METHOD AND SYSTEM, AND MEDIUM

(71) Applicants: BOE TECHNOLOGY GROUP CO., LTD., Beijing (CN); PEKING UNIVERSITY, Beijing (CN)

(72) Inventors: Hongwen Zhu, Beijing (CN); Li Zhou, Beijing (CN); Yafei Dai, Beijing (CN); Xue Chen, Beijing (CN); Shengpeng Zou, Beijing (CN); Yiping Song, Beijing (CN); Ming Zhang, Beijing (CN); Zihan Zhang, Beijing (CN); Wei Ju, Beijing (CN)

(73) Assignees: BOE TECHNOLOGY GROUP CO., LTD., Beijing (CN); PEKING UNIVERSITY, Beijing (CN)

( * ) Notice: Subject to any disclaimer, the term of this patent is extended or adjusted under 35 U.S.C. 154(b) by 1094 days.

(21) Appl. No.: 17/413,373

(22) PCT Filed: May 9, 2020

(86) PCT No.: PCT/CN2020/089394
§ 371 (c)(1),
(2) Date: Jun. 11, 2021

(87) PCT Pub. No.: WO2020/228636
PCT Pub. Date: Nov. 19, 2020

(65) Prior Publication Data
US 2022/0092441 A1 Mar. 24, 2022

(30) Foreign Application Priority Data
May 10, 2019 (CN) .......................... 201910390546.5

(51) Int. Cl.
*G06V 10/82* (2022.01)
*G06F 18/20* (2023.01)
(Continued)

(52) U.S. Cl.
CPC .......... *G06V 10/82* (2022.01); *G06F 18/2155* (2023.01); *G06F 18/29* (2023.01); *G06N 5/02* (2013.01); *G16H 10/20* (2018.01)

(58) Field of Classification Search
CPC ........ G06V 10/82; G16H 10/20; G06F 18/29; G06F 18/2155; G06F 16/90332; G06N 5/02
See application file for complete search history.

(56) References Cited

U.S. PATENT DOCUMENTS

| | | | | |
|---|---|---|---|---|
| 10,387,463 | B2 * | 8/2019 | Campbell | ............. G10L 15/063 |
| 2013/0262349 | A1 * | 10/2013 | Bouqata | ................. G06N 20/10 |
| | | | | 706/12 |

(Continued)

FOREIGN PATENT DOCUMENTS

| | | |
|---|---|---|
| CN | 107342078 A | 11/2017 |
| CN | 107911299 A | 4/2018 |

(Continued)

OTHER PUBLICATIONS

NPL: Oh, Kyo-Joong, et al. "A chatbot for psychiatric counseling in mental healthcare service based on emotional dialogue analysis and sentence generation." (2017). (Year: 2017).*

(Continued)

*Primary Examiner* — Li B. Zhen
*Assistant Examiner* — Sadik A Alshahari

(57) ABSTRACT

Disclosed are a reinforcement learning model training method and apparatus, a dialogue processing method and a dialogue system, and a computer-readable storage medium. The reinforcement learning model training method includes:
(Continued)

acquiring unlabelled data and labelled data which are used for training a reinforcement learning model; on the basis of the unlabelled data, generating, with reference to the labelled data, an experience pool for training the reinforcement learning model; and using the experience pool to train the reinforcement learning model.

11 Claims, 8 Drawing Sheets

(51) Int. Cl.
 *G06F 18/214* (2023.01)
 *G06N 5/02* (2023.01)
 *G16H 10/20* (2018.01)

(56) References Cited

U.S. PATENT DOCUMENTS

| | | | | |
|---|---|---|---|---|
| 2017/0235912 | A1* | 8/2017 | Moturu | G16H 40/67 |
| | | | | 705/2 |
| 2018/0046773 | A1* | 2/2018 | Tang | G06N 3/044 |
| 2019/0014488 | A1* | 1/2019 | Tan | G06N 3/044 |
| 2019/0115027 | A1* | 4/2019 | Shah | G10L 17/22 |
| 2019/0311814 | A1* | 10/2019 | Kannan | G16H 10/60 |
| 2019/0348178 | A1* | 11/2019 | Eleftherou | G16H 50/50 |
| 2019/0355471 | A1* | 11/2019 | Peng | G06N 3/006 |
| 2019/0385091 | A1* | 12/2019 | Munawar | G06N 7/01 |
| 2020/0043610 | A1* | 2/2020 | Al Hasan | G16H 50/20 |
| 2020/0058399 | A1* | 2/2020 | Chen | G06N 3/08 |
| 2020/0098476 | A1* | 3/2020 | Loscutoff | G16H 50/70 |
| 2020/0226475 | A1* | 7/2020 | Ma | G06F 40/30 |
| 2020/0303068 | A1* | 9/2020 | Osogami | G06N 20/00 |
| 2022/0036180 | A1* | 2/2022 | Archuleta | G06N 7/01 |

FOREIGN PATENT DOCUMENTS

| | | | | | |
|---|---|---|---|---|---|
| CN | 108090218 A | * | 5/2018 | | G06F 16/3329 |
| CN | 108600379 A | | 9/2018 | | |
| CN | 109710741 A | | 5/2019 | | |

OTHER PUBLICATIONS

NPL: Mohammadi, Mehdi, et al. "Semi-supervised Deep Reinforcement Learning in Support of IoT and Smart City Services." (2018). (Year: 2018).*

NPL: Finn, Chelsea, et al. "Generalizing skills with semi-supervised reinforcement learning." (2017). (Year: 2017).*

* cited by examiner

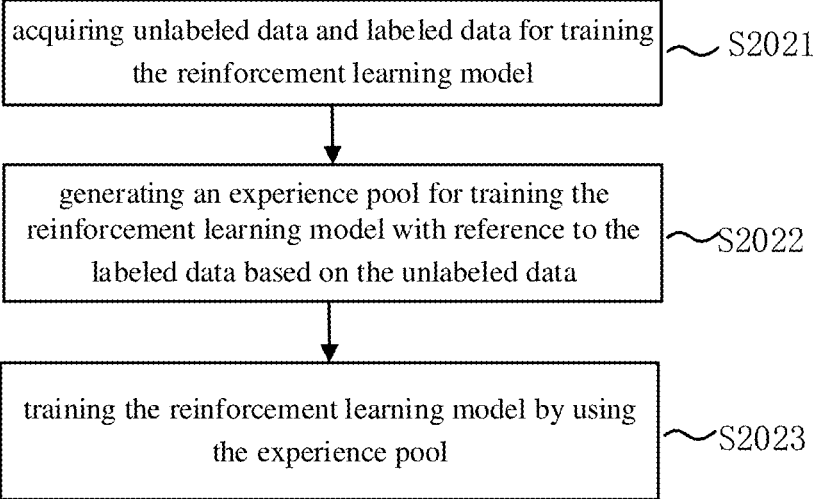

acquiring unlabeled data and labeled data for training the reinforcement learning model ~ S2021 generating an experience pool for training the reinforcement learning model with reference to the labeled data based on the unlabeled data ~ S2022 training the reinforcement learning model by using the experience pool ~ S2023

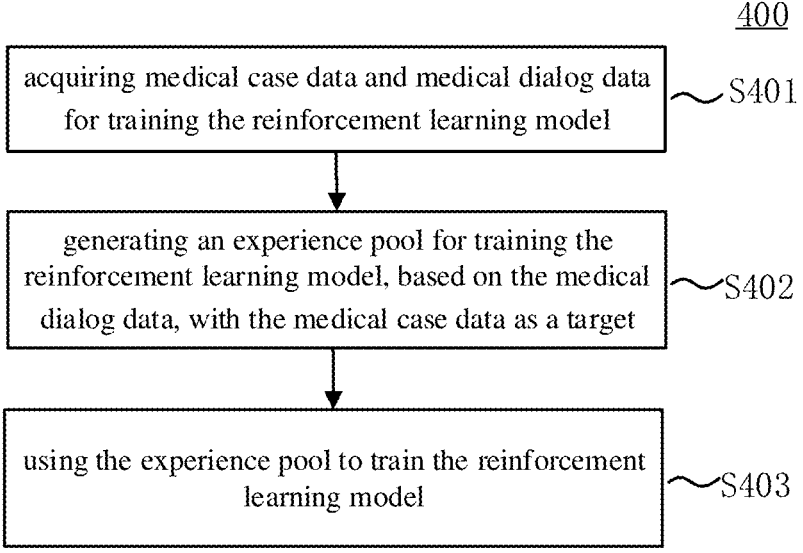

acquiring medical case data and medical dialog data for training the reinforcement learning model ~ S401 generating an experience pool for training the reinforcement learning model, based on the medical dialog data, with the medical case data as a target ~ S402 using the experience pool to train the reinforcement learning model ~ S403

FIG. 4

```
{
    "disease_tag": "Ischaemic heart diseases",
    "request_slots": {
        "disease": "UNK"
    },
     "goal": {
          "explicit_symptoms": {
                "palpitation": {"frequency": "occasional"},
                "sweatiness": {"condition": "after exercise"}
          },
          "implicit_symptoms": {
                 "chest distress": {"performance": "aggravation"},
                 "fever": {"t/f": false},
                 "emesis": {"occur": "a few weeks ago"}
          }
       }
}
```

FIG. 5

TRAINING METHOD AND APPARATUS, DIALOGUE PROCESSING METHOD AND SYSTEM, AND MEDIUM

This application is a National Stage of International Application No. PCT/CN2020/089394, filed May 9, 2020, which claims the benefit of foreign priority of Chinese Patent Application No. 201910390546.5, filed on May 10, 2019, the entireties of which are hereby incorporated herein by reference.

TECHNICAL FIELD

The present disclosure relates to the field of machine learning, in particular to a method and an apparatus for training a reinforcement learning model, a dialog processing method, a dialog system, and a computer-readable storage medium.

BACKGROUND

Reinforcement learning, also known as reinforcement learning and evaluation learning, is an important machine learning method, which is widely used in fields such as intelligent robot control and analysis and prediction. Reinforcement learning refers to that an agent learns in a "trial-and-error" manner, the reward score obtained by interacting with the environment guides behaviors, and the goal is to make the behavior selected by the agent get the maximum reward score for the environment.

A dialog system, or conversation agent, is a computer system that aims to communicate with people coherently, which may include a computer-based agent having a man-machine interface for accessing, processing, managing, and transmitting information. A dialog system can be implemented based on a reinforcement learning model. However, in the process of constructing a dialog system based on a reinforcement learning model, it is required generally to obtain a large amount of labeled data so as to improve the accuracy of the dialog system. The required labeled data is usually expensive and difficult to obtain, thus affecting the training and construction of the reinforcement learning model, also limiting the further application of the dialog system in various fields.

SUMMARY

According to one aspect of the present disclosure, there is provided a method for training a reinforcement learning model, which includes: acquiring unlabeled data and labeled data for training the reinforcement learning model; generating an experience pool for training the reinforcement learning model with reference to the labeled data, based on the unlabeled data; and training the reinforcement learning model by using the experience pool.

According to another aspect of the present disclosure, there is provided a dialog processing method, which includes: acquiring dialog information; generating reply information based on a reinforcement learning model; responding to the dialog information based on the reply information. The reinforcement learning model is trained by: acquiring unlabeled data and labeled data for training the reinforcement learning model; generating an experience pool for training the reinforcement learning model with reference to the labeled data, based on the unlabeled data; and training the reinforcement learning model by using the experience pool.

According to another aspect of the present disclosure, there is provided a training apparatus for a reinforcement learning model, which includes: an acquiring unit configured to acquire unlabeled data and labeled data for training the reinforcement learning model; a generating unit configured to generate an experience pool for training the reinforcement learning model with reference to the labeled data, based on the unlabeled data; and a training unit configured to train the reinforcement learning model by using the experience pool.

According to another aspect of the present disclosure, there is provided a training apparatus for a reinforcement learning model, which includes: a processor, a memory, and computer program instructions stored in the memory. When the instructions are executed by the processor, cause the processor to: acquire unlabeled data and labeled data for training the reinforcement learning model; generate an experience pool for training the reinforcement learning model with reference to the labeled data, based on the unlabeled data; and train the reinforcement learning model by using the experience pool.

According to another aspect of the present disclosure, there is provided a computer-readable storage medium having computer-readable instructions stored thereon, and when the instructions are executed by a computer, the method for training a reinforcement learning model according to any one of the embodiments is executed.

According to another aspect of the present disclosure, there is provided a dialog system, which includes: an acquiring unit configured to acquire dialog information; a generating unit configured to generate reply information based on a reinforcement learning model; and a responding unit configured to respond to the dialog information based on the reply information. The reinforcement learning model is trained by: acquiring unlabeled data and labeled data for training the reinforcement learning model; generating an experience pool for training the reinforcement learning model with reference to the labeled data, based on the unlabeled data; and training the reinforcement learning model by using the experience pool.

According to another aspect of the present disclosure, there is provided a dialog system which includes: a processor; a memory; and computer program instructions stored in the memory. When the computer program instructions are executed by the processor, cause the processor to acquire dialog information; generate reply information based on a reinforcement learning model; and respond to the dialog information based on the reply information. The reinforcement learning model is trained by: acquiring unlabeled data and labeled data for training the reinforcement learning model; generating an experience pool for training the reinforcement learning model with reference to the labeled data, based on the unlabeled data; and training the reinforcement learning model by using the experience pool.

According to another aspect of the present disclosure, there is provided a computer-readable storage medium having computer-readable instructions stored thereon. When the instructions are executed by a computer, the dialog processing method according to any one of the embodiments is executed.

BRIEF DESCRIPTION OF THE DRAWINGS

In order to more clearly describe the technical schemes of the embodiments of the present disclosure, the following will briefly introduce the drawings that need to be used in the description of the embodiments. Obviously, the drawings in the following description are only some embodiments of the present disclosure. For those of ordinary skill in the art, without creative work, other drawings can be obtained from these drawings. The following drawings are not deliberately scaled to the actual size, and the purpose is to illustrate the gist of the present disclosure.

FIG. 3 illustrates an exemplary flowchart of a method for training a reinforcement learning model used in a dialog processing method according to some embodiments of the present disclosure;

FIG. 4 illustrates an exemplary flowchart of a method for training a reinforcement learning model for a medical dialog system according to some embodiments of the present disclosure;

FIG. 5 illustrates a schematic diagram of target information in a method for training a reinforcement learning model for a medical dialog system according to some embodiments of the present disclosure;

DETAILED DESCRIPTION

Figure 1:
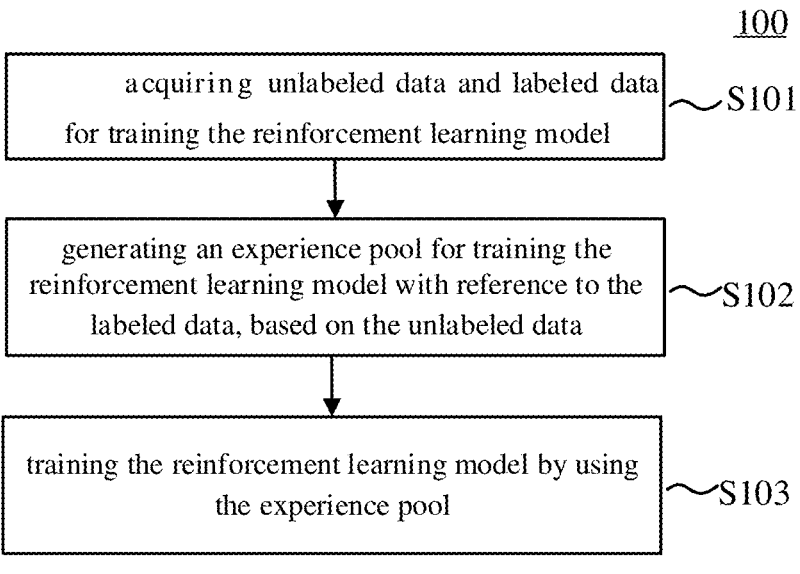
FIG. 1 illustrates an exemplary flowchart of a method for training a reinforcement learning model according to some embodiments of the present disclosure.

The technical schemes in the embodiments of the present disclosure will be clearly and completely described below in conjunction with the drawings. Obviously, the described embodiments are only part of the embodiments of the present disclosure, rather than all of the embodiments. Based on the embodiments of the present disclosure, all other embodiments obtained by those of ordinary skill in the art without inventive work also fall within the scope of the present disclosure.

As illustrated in the present disclosure and claims, unless the context clearly indicates exceptional cases, the words such as "a," "an," "one," and/or "the" do not specifically refer to the singular, but may also include the plural. In general, the terms such as "include/including" and "comprise/comprising" only indicate that the clearly identified steps and elements are included, and these steps and elements do not constitute an exclusive list. A method, apparatus, or system may also include other steps or elements.

Although the present disclosure makes various references to certain modules in the apparatus and system according to the embodiments of the present disclosure, any number of different modules may be used and executed on a client and/or server. The modules are only illustrative, and different modules may be used for different aspects of the apparatus, system, and method.

Flowcharts are used in the present disclosure to illustrate operations performed by the apparatus and system according to the embodiments of the present disclosure. It should be understood that the preceding or following operations are not necessarily performed exactly in order. On the contrary, the various operations may be processed in reverse order or simultaneously as required. Of course, other operations may be added to these processes, or one operation or several operations may be removed from these processes.

Generally, a reinforcement learning model includes an agent and environment, and the agent continuously learns through interaction and feedback with the environment and optimizes its strategy. Specifically, the agent observes and obtains a state (represented as s) of the environment, and determines a behavior or an action (represented as a) to be taken for the current state (s) of the environment according to a certain strategy. This action (a) acts on the environment, the state of the environment would be changed (for example, from s to s'), and meanwhile a reward score (represented as r) would be generated as feedback sent to the agent. The agent determines whether the previous action is correct according to the reward score (r) that is obtained, and whether the strategy needs to be adjusted, and further updated. By repeatedly observing the state, determining the action, and receiving the feedback, the agent can continuously update the strategy. The ultimate goal of the training of the reinforcement learning model is to learn a strategy that maximizes the accumulation of reward scores. In the reinforcement learning process of learning and adjusting strategies, the agent may adopt some deep learning algorithms including neural networks, such as neural networks based on deep reinforcement learning DRL (such as deep Q-learing (DQN), double-DQN, dualing-DQN, deep deterministic policy gradient (DDPG), asynchronous advantage actor-critic (A3C), continuous deep Q-learning with NAF, etc.). The reinforcement learning model described in the embodiments of the present disclosure may be a neural network based on deep reinforcement learning DRL.

It can be seen that in the training process of the reinforcement learning model, a large amount of labeled data is generally required to be used as training targets to guide the training process. However, the acquisition of the labeled data often consumes a lot of time and system resources, and the amount of the labeled data is small, which is difficult to obtain.

On this basis, the embodiments of the present disclosure provide a method for training a reinforcement learning model, as illustrated in FIG. 1. FIG. 1 illustrates an exemplary flowchart of a method 100 for training a reinforcement learning model according to some embodiments of the present disclosure. Optionally, the reinforcement learning model involved in FIG. 1 may be applied to many fields such as education, legal consultation, shopping and dining inquiries, flight inquiries, navigation, etc.

In step S101, unlabeled data and labeled data for training the reinforcement learning model are acquired.

In this step, the acquired data for training the reinforcement learning model includes labeled data. Optionally, the labeled data may be data acquired from a database which is related to the field of the reinforcement learning model to be trained. In an example, training information related to the reinforcement learning model may be extracted from the labeled data, and the extracted training information may be saved as, for example, target information of a user (also known as a user goal). The target information extracted from the labeled data can be used for direct training of the reinforcement learning model so as to provide feedback to the agent and guide the training process. Optionally, the target information extracted from the labeled data may include information corresponding to a result, a classification tag, etc., respectively.

Further, the acquired data for training the reinforcement learning model may also include unlabeled data. Optionally, the unlabeled data may be acquired through various manners, and these manners may include unlabeled web pages, forums, chat records, databases, etc. related to the field of the reinforcement learning model to be trained. Optionally, the unlabeled data may be dialog data. In an example, it is also possible to extract training information related to the reinforcement learning model from the unlabeled data, and use the extracted training information to subsequently generate an experience pool for training the reinforcement learning model.

Optionally, in the case where the method of the embodiments of the present disclosure is applied to the medical field, the labeled data may be medical case data obtained from, for example, electronic medical records, and the extracted target information may include various information such as diseases, symptom classifications, symptom attributes. Correspondingly, the unlabeled data may be, for example, medical dialog data obtained from the Internet, and the extracted training information of the unlabeled data may include various information such as dialog time, dialog objects, dialog content, diagnostic results. Of course, the above content is for example only. In the embodiments of the present disclosure, the training method can also be applied to various other fields such as education, legal consultation, shopping and dining inquiries, flight inquiries, navigation, etc., which are not limited here.

In step S102, an experience pool for training the reinforcement learning model is generated with reference to the labeled data, based on the unlabeled data.

In this step, optionally, the experience pool is generated based on the effective training information extracted from the unlabeled data, with the target information extracted from the labeled data being as the training target. Optionally, the experience pool may include one or more sequences consisting of a first state (s), an action (a), a reward score (r), and a second state (s'), each of which may be represented as a quadruple <s, a, r, s'>. In an example, the action and the first state that is current can be obtained based on the unlabeled data, and the second state and the reward score can be obtained through interaction with the environment. When the unlabeled data is dialog data, the action may be any dialog action acquired based on the dialog data, the first state may include all historical information in the dialog data which is before the acquired dialog action, and the historical information may be composed of all information and actions before the dialog action. Correspondingly, the second state may be the state that the environment migrates to after the action is applied in the case where the environment is in the first state, and the reward score may include feedback made under the guidance of the labeled data which serves as the target information, after the action is applied in the case the environment is in the first state.

Optionally, the reward score in the quadruple for constructing the experience pool may further include the credibility (c or c') of the action. In other words, in the case where the field of the reinforcement learning model to be trained is known, based on the action (a), the corresponding occurrence probability and specificity thereof in the key information set of the field can be calculated, so as to obtain the credibility (c) of the action, and the processed credibility (c') is obtained after smoothing and normalization processing on the credibility (c). Subsequently, the experience pool can be constructed according to the quadruple <s, a, c'r, s'>.

Optionally, in the case where the method of the embodiments of the present disclosure is applied to the medical field, the action and the first state that is current may be acquired based on medical dialog data, and the second state and the reward score may be acquired through interaction with the environment. The action may be any dialog action acquired based on the medical dialog data. For example, the action includes but is not limited to: starting a dialog, ending a dialog, requesting symptom information, diagnosing a disease, etc., the first state may include all historical information in the medical dialog data which is before the acquired dialog action, and the historical information may be composed of all the information and actions before the dialog action. Correspondingly, the second state may be the state that the environment migrates to after the action is applied in the case where the environment is in the first state; the reward score may include the feedback made under the guidance of the medical case data which serves as the target information, after the action is applied in the case the environment is in the first state. Optionally, in this case, the credibility of the action included in the reward score can be calculated by the following formulas (1)-(3):

$$AF = \frac{\text{count}((a, d_j^i) \mid d_j^i \in D^i)}{|\{d_j^i\}|} \quad (1)$$

$$IDF = \log\frac{|\{D^i\}|}{\text{count}((a, D^i) \mid \exists d_j^i \in D^i, a \in d_j^i)} \quad (2)$$

$$AF - IDF = AF \cdot IDF \quad (3)$$

where $D=\{D^i\}$ may be a set of diseases, and the set of diseases can include, for example, several diseases encoded by ICD-10. For example, $D^i$ may represent the $i^{th}$ disease (i is 0 or a positive integer), and each disease $D^i$ may include several pieces of medical dialog data. For example, $$d_j^i$$

may represent the $j^{th}$ piece of dialog data for disease $D^i$ (j is 0 or a positive integer), then AF may represent the probability that action (a) appears in the medical dialog data $$d_j^i,$$

IDF represents the specificity that action (a) appears in a specific disease. Therefore, the credibility AF-IDF can be obtained by the product of AF and IDF both, so as to reflect the credibility (c) of a certain action (a). After the credibility (c) is calculated, the processed credibility (c') is obtained after smoothing and normalization processing on the credibility (c), so as to avoid affecting the training results because of some uncollected diseases. Finally, the quadruple <s, a, c'r, s'> can be formed according to the calculated c' so as to construct the experience pool.

In step S103, the experience pool is used to train the reinforcement learning model.

In the embodiments of the present disclosure, after the experience pool is formed according to unlabeled data and labeled data, the experience pool may be used to assist in training the reinforcement learning model. Optionally, the agent (for example, DQN neural network) and the environment (for example, a user simulator) can interact. During the interaction, the quadruple (<s, a, r, s'> or <s, a, c'r, s'>) included in the experience pool is used to assist in training, and the labeled data or the target information extracted from the labeled data serves as the training target, so as to update parameters in DQN through continuous simulation and iteration, thereby obtaining the final training results. Optionally, in the process of training, the experience pool may be continuously updated by using the quadruple obtained in the process of training, that is, the new quadruple obtained in the process of training can be added to the experience pool. Therefore, using the experience pool to train the reinforcement learning model may further include: in the process of training the reinforcement learning model, updating the experience pool according to the training results, and using the updated experience pool to train the reinforcement learning model. In the process of training the reinforcement learning model, the action (a) in the formed quadruple can be initiated by the DQN and can act on the environment, instead of being obtained from unlabeled data. In the medical field, for example, the action in this case may also include but is not limited to: starting a dialog, ending a dialog, requesting symptom information, diagnosing a disease, etc.

Optionally, in the embodiments of the present disclosure, when training the reinforcement learning model, external knowledge may be introduced additionally to assist decision-making. In this case, the training results of the reinforcement learning model and the content of the external knowledge can be considered simultaneously, in order to make the final decision and achieve the purpose of further improving the training effect of the reinforcement learning model. In one example, the external knowledge herein may be a database related to the reinforcement learning model, such as a knowledge graph. For example, in the case of training the reinforcement learning model of a medical dialog system, the knowledge graph includes nodes of M diseases and N symptoms and the corresponding relationships between various diseases and various symptoms (where M and N are integers greater than or equal to 1), and recommended drugs, preventive measures, treatment schemes, etiology, and so on, for each disease. Optionally, the knowledge graph may also include the probability of each disease relative to each symptom and the probability of each symptom relative to each disease. In the embodiments of the present disclosure, optionally, the method for training the reinforcement learning model may be used to train a reinforcement learning model for a dialog system. According to different task types of the dialog system, the dialog system may be classified as a task-oriented dialog system and a non-task-oriented dialog system. The task-oriented dialog system refers to a type of a dialog system that aims to help users complete tasks in a specific field based on communication with users. In one example, the method for training the reinforcement learning model can be used to train a reinforcement learning model for a task-oriented dialog system, for example, can be used to train a reinforcement learning model for a medical dialog system. Of course, the above content is only for example. In the embodiments of the present disclosure, the method can also be applied to dialog systems related to various other fields such as education, legal consultation, shopping and dining inquiries, flight inquiries, navigation, etc., which are not limited here.

According to the method for training a reinforcement learning model in the embodiments of the present disclosure, the reinforcement learning model can be jointly trained based on unlabeled data and labeled data, thereby effectively reducing the requirements for labeled data during the training of the reinforcement learning model, improving the feasibility and stability of the training of the reinforcement learning model, and improving the training results of the reinforcement learning model.

Figure 2:
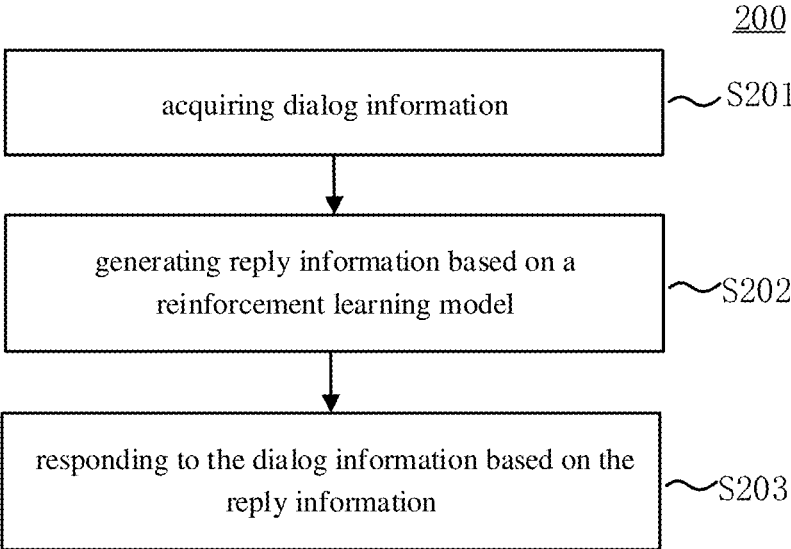
FIG. 2 illustrates an exemplary flowchart of a dialog processing method according to some embodiment of the present disclosure.

The embodiments of the present disclosure provide a dialog processing method, as illustrated in FIG. 2. FIG. 2 illustrates an exemplary flowchart of a dialog processing method 200 according to the embodiments of the present disclosure. The dialog processing method in FIG. 2 can be applied to a dialog system, also known as chat information system, spoken dialog system, conversation agent, chatter robot, chatterbot, chatbot, chat agent, digital personal assistant, and automated online assistant, etc. The dialog system can use natural language to interact with people so as to simulate intelligent conversations and provide personalized assistance to users. The dialog system can be implemented based on a reinforcement learning model. Optionally, the reinforcement learning model on which the method illustrated in FIG. 2 is based can be applied to many fields such as education, legal consultation, shopping and dining inquiries, flight inquiries, navigation and so on.

In step S201, dialog information is acquired.

In this step, the acquired dialog information may be, for example, natural language text. Optionally, the dialog information can be understood based on the natural language text, and the effective dialog information to be processed can be extracted therefrom through various operations such as word segmentation, semantic analysis, etc., for use in subsequent dialog processing procedures.

In step S202, reply information is generated based on a reinforcement learning model.

In this step, according to the acquired dialog information, based on, for example, a reinforcement learning model of DQN, the reply information that needs to be fed back can be generated. The reinforcement learning model may be obtained by training according to the method for training a reinforcement learning model above.

FIG. 3 illustrates an exemplary flowchart of a method for training a reinforcement learning model used in a dialog processing method according to some embodiments of the present disclosure. Optionally, the reinforcement learning model involved in FIG. 3 can be applied to many fields such as education, legal consultation, shopping and dining inquiries, flight inquiries, navigation and so on.

In step S2021, unlabeled data and labeled data for training the reinforcement learning model are acquired.

In this step, the acquired data used for training the reinforcement learning model includes labeled data. Optionally, the labeled data may be data obtained from a database related to the field of the reinforcement learning model to be trained. In one example, training information related to the reinforcement learning model may be extracted from the labeled data, and the extracted training information may be saved as, for example, target information of the user (also known as the user goal). The extracted target information from the labeled data can be used for direct training of the reinforcement learning model so as to provide feedback to the agent and guide the training process. Optionally, the target information extracted from the labeled data may include information corresponding to a result (result), a classification tag (tag), etc., respectively.

Further, the acquired data used for training the reinforcement learning model may also include unlabeled data. Optionally, the unlabeled data may be obtained through various manners, and these manners may include unlabeled web pages, forums, chat records, databases, and others related to the field of the reinforcement learning model to be trained. Optionally, the unlabeled data may be dialog data. In one example, it is also possible to extract training information related to the reinforcement learning model from unlabeled data, and use the extracted training information to subsequently generate an experience pool for training the reinforcement learning model.

Optionally, in the case where the method of the embodiments of the present disclosure is applied to the medical field, the labeled data may be medical case data obtained from, for example, electronic medical records, and the extracted target information may include various information such as diseases, symptom classifications, and symptom attributes. Correspondingly, the unlabeled data may be, for example, medical dialog data obtained from the Internet, and the extracted training information of the unlabeled data may include various information such as dialog time, dialog objects, dialog content, and diagnostic results. Of course, the above content is only for example. In the embodiments of the present disclosure, the method for training can also be applied to various other fields such as education, legal consultation, shopping and dining inquiries, flight inquiries, navigation, etc., which are not limited here.

In step S2022, an experience pool for training the reinforcement learning model is generated with reference to the labeled data based on the unlabeled data.

In this step, optionally, the experience pool may be generated, with the target information extracted from the labeled data being as the training target, based on effective training information extracted from the unlabeled data. Optionally, the experience pool may include one or more sequences consisting of a first state (s), an action (a), a reward score (r), and a second state (s'), and may be represented as a quadruple <s, a, r, s'>. In one example, the action and the first state which is current can be obtained based on unlabeled data, and the second state and the reward score can be obtained through interaction with the environment. In the case where the unlabeled data is dialog data, the action may be any dialog action acquired based on the dialog data, the first state may include all historical information in the dialog data which is before the acquired dialog action, and the historical information may be composed of all the information and actions before the dialog action. Correspondingly, the second state may be the state that the environment migrates to after the action is applied in the case where the environment is in the first state, and the reward score may include the feedback made under the guidance of the labeled data which serves as the target information after the action is applied in the case the environment is in the first state.

Optionally, the reward score in the quadruple used for constructing the experience pool may further include the credibility (c or c') of the action. In other words, in the case where the field of the reinforcement learning model to be trained is known, based on the action (a), the corresponding occurrence probability and specificity thereof in the key information set of the field can be calculated, so as to obtain the credibility (c) of the action, and the processed credibility (c') is obtained after smoothing and normalization processing on the credibility (c). Subsequently, the experience pool can be constructed according to the quadruple <s, a, c'r, s'>.

Optionally, in the case where the method of the embodiments of the present disclosure is applied to the medical field, the action and the first state that is current may be acquired based on medical dialog data, and the second state and the reward score may be acquired through interaction with the environment. The action may be any dialog action acquired based on the medical dialog data. For example, the action includes but is not limited to: starting a dialog, ending a dialog, requesting symptom information, diagnosing a disease, etc., the first state may include all historical information in the medical dialog data which is before the acquired dialog action, and the historical information may be composed of all the information and actions before the dialog action. Correspondingly, the second state may be the state that the environment migrates to after the action is applied in the case where the environment is in the first state; and the reward score may include the feedback made under the guidance of the medical case data which serves as the target information, after the action is applied in the case the environment is in the first state. Optionally, in this case, the credibility of the action included in the reward score can be calculated by the formulas (1)-(3) mentioned above.

Where D={D$^i$} may be a set of diseases, and the set of diseases can include, for example, several diseases encoded by ICD-10. For example, D$^i$ may represent the i$^{th}$ disease (i is 0 or a positive integer), and each disease D$^i$ may include several pieces of medical dialog data. For example, $$d^i_j$$

may represent the j$^{th}$ dialog data for disease D$^i$ (j is 0 or a positive integer), then AF may represent the probability that action (a) appears in the medical dialog data $$d^i_j,$$

IDF represents the specificity that action (a) appears in a specific disease. Therefore, the credibility AF-IDF can be obtained by the product of AF and IDF both, so as to reflect the credibility (c) of a certain action (a). After the credibility (c) is calculated, the processed credibility (c') is obtained after smoothing and normalization processing on the credibility (c), so as to avoid affecting the training results because of some uncollected diseases. Finally, the quadruple <s, a, c'r, s'> can be formed according to the calculated c' so as to construct the experience pool.

In step S2023, the experience pool is used to train the reinforcement learning model.

In the embodiments of the present disclosure, after the experience pool is formed according to unlabeled data and labeled data, the experience pool may be used to assist in training the reinforcement learning model. Optionally, the agent (for example, DQN neural network) and the environment (for example, a user simulator) can interact. During the interaction, the quadruple (<s, a, r, s'> or <s, a, c'r, s'>) included in the experience pool is used to assist in training, and the labeled data or the target information extracted from the labeled data serves as the training target, so as to update parameters in DQN through continuous simulation and iteration, thereby obtaining the final training results. Optionally, in the process of training, the experience pool may be continuously updated by using the quadruple obtained in the process of training, that is, the new quadruple obtained in the process of training can be added to the experience pool. Therefore, using the experience pool to train the reinforcement learning model may further include: in the process of training the reinforcement learning model, updating the experience pool according to the training results, and using the updated experience pool to train the reinforcement learning model. In the process of training the reinforcement learning model, the action (a) in the formed quadruple can be initiated by the DQN and can act on the environment. In the medical field, for example, the action in this case may also include but is not limited to: starting a dialog, ending a dialog, requesting symptom information, diagnosing a disease, etc.

Optionally, in the embodiments of the present disclosure, when training the reinforcement learning model, external knowledge may be introduced additionally to assist decision-making. In this case, the training results of the reinforcement learning model and the content of the external knowledge can be considered simultaneously, in order to make the final decision and achieve the purpose of further improving the training effect of the reinforcement learning model. In one example, the external knowledge herein may be a database related to the reinforcement learning model, such as a knowledge graph, etc.

Returning to FIG. 2, in step S203, a response is made to the dialog information based on the reply information.

In this step, the reply information generated by the trained DQN can be converted into natural language and output, so as to respond to the dialog information.

According to the dialog processing method of the embodiments of the present disclosure, the reinforcement learning model can be jointly trained based on unlabeled data and labeled data, thereby effectively reducing the requirements for the labeled data during the training of the reinforcement learning model, improving the feasibility and stability of the training of the reinforcement learning model, and improving the training results of the reinforcement learning model.

First Example

In the first example of the embodiments of the present disclosure, a method for training a reinforcement learning model for a medical dialog system is provided, as illustrated in FIG. 4. FIG. 4 illustrates an exemplary flowchart of a method 400 for training a reinforcement learning model for a medical dialog system according to some embodiments of the present disclosure.

In step S401, medical case data and medical dialog data for training the reinforcement learning model are acquired.

In this step, the acquired data for training the reinforcement learning model may include medical case data acquired from electronic medical records. On this basis, the target information as the user goal can be extracted from the medical case data, for example, the target information may include various information such as diseases, symptom classifications, symptom attributes, and so on.

For example, the target information can be extracted according to the format illustrated in FIG. 5. In FIG. 5, the diseases can be represented as "disease_tag:" ischaemic heart diseases. The symptoms actively reported by the patient can be recorded in "explicit_symptoms." For example, in FIG. 5, the symptoms include "palpitations" with the frequency being "occasional," and "sweatiness" with the condition being "after exercise." After the inquiry of the doctor, the symptoms obtained from the subsequent dialog can be recorded in "implicit_symptoms." For example, in FIG. 5, the symptoms include "chest distress" with the performance "aggravation," and "emesis" which occurs at "a few weeks ago," without "fever." In FIG. 5, the remaining tags of the target information may be unknown, which are denoted as "UNK."

Correspondingly, the unlabeled data may be, for example, medical dialog data obtained from the Internet, and the training information of the unlabeled data extracted therefrom may include various information such as dialog time, dialog objects, dialog content, diagnostic results, etc., which can be saved as, for example, a JSON file.

In step S402, based on the medical dialog data, with the medical case data being as target information, an experience pool for training the reinforcement learning model is generated.

Figure 6:
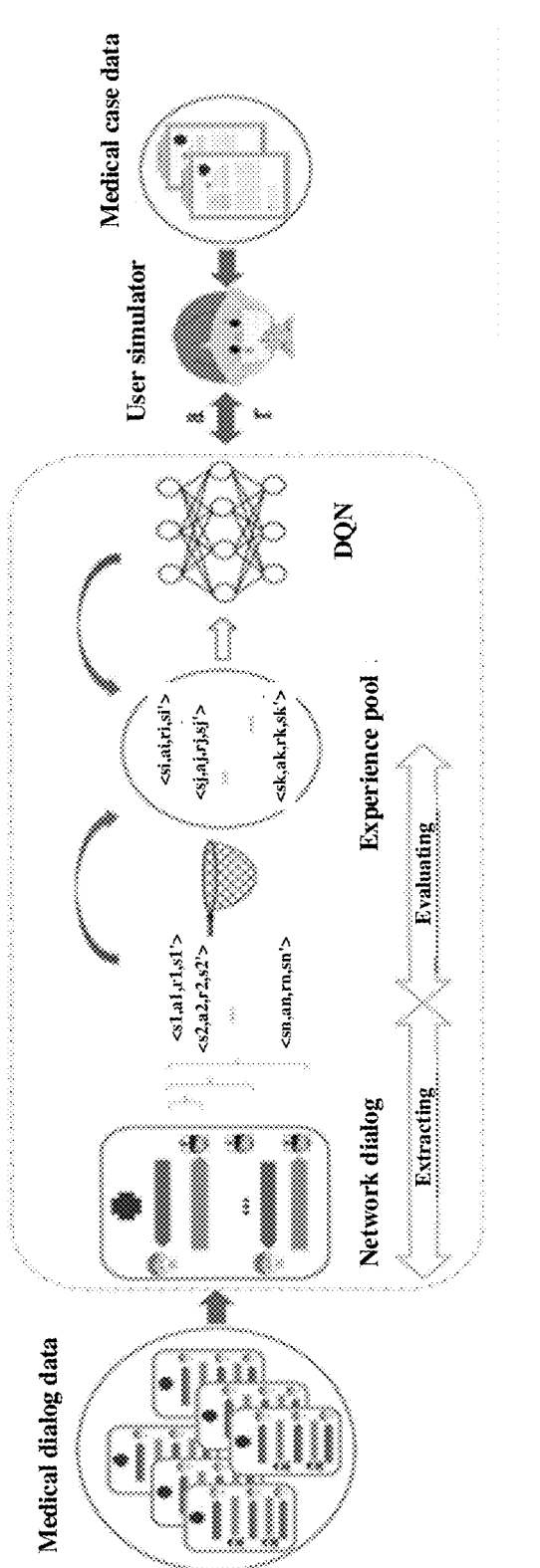
FIG. 6 illustrates a schematic diagram of data collected according to the first example of the present disclosure and a training process for DQN.

FIG. 6 illustrates a schematic diagram of the data collected according to the first example of the present disclosure and the training process of the DQN. As illustrated in FIG. 6, the left side is unlabeled data, that is, medical dialog data, which is expressed in the format of network dialog, and the right side is labeled data, that is, medical case data, which serves as the target information (the user goal) and is used for the subsequent training process of the DQN. In FIG. 6, the effective training information may be extracted based on the medical dialog data first, and the target information extracted from the labeled data may serve as the training target, and the experience pool can be generated through interactions with the environment (user simulator).

Specifically, any of the dialog actions acquired based on the medical dialog data can serve as the action (a), for example, the action (a) includes but is not limited to: starting a dialog, ending a dialog, requesting symptom information, diagnosing a disease, etc., and all information and actions in the medical dialog data which are before the action (a) are combined to compose historical information so as to form the first state (s). Correspondingly, the second state may be the state (s') to which the environment migrates after the action (a) is applied in the case where the user simulator is in the first state (s), and the reward score may include the feedback (r) made under the guidance of the medical case data which serves as the target information, after the action (a) is applied in the case where the user simulator is in the first state (s). In this case, the experience pool may be constructed according to the quadruple $<s, a, r, s'>$.

Specifically, as illustrated in FIG. 6, multiple quadruples may be formed according to the medical dialog data, for example, $<s1, a1, r1, s1'>$ to $<sn, an, rn, sn'>$, for constructing subsequently the experience pool. In the process of constructing the experience pool, the multiple quadruples previously formed may be evaluated and selected. Optionally, these quadruples, for example, $<si, ai, ri, si'>$, $<sj, aj, rj, sj'>$ to $<sk, ak, rk, sk'>$ can be used to construct the experience pool. Of course, the method for constructing the experience pool is only for example, and optionally, all the first-$n^{th}$ quadruples can also be provided in the experience pool.

In addition, in another example, the action can also be further evaluated using credibility. In other words, the reward score may also include the credibility (c') of the action (a). That is, based on the action (a), the corresponding occurrence probability and specificity of the action (a) in the set of diseases $D=\{D^i\}$ in the medical field can be calculated, so as to obtain the credibility (c) of the action, and the processed credibility (c') is obtained after smoothing and normalization processing on the credibility (c). Subsequently, the experience pool can also be constructed according to the quadruple <s, a, c'r, s'>, and the specific example is not illustrated in FIG. 6.

In step S403, the experience pool is used to train the reinforcement learning model.

In the first example of the present disclosure, after the experience pool is generated according to the medical dialog data and the medical case data, the experience pool may be used to assist in training the reinforcement learning model. Optionally, the DQN in FIG. 6 and the user simulator can interact. During the interaction, the quadruple contained in the experience pool is used to assist in training, and the target information (the user goal) serves as the training target, so as to update parameters in DQN through continuous simulation and iteration, thereby obtaining the final training results. Optionally, in the process of training, the experience pool may be continuously updated by using the quadruple obtained in the process of training, that is, the new quadruple obtained in the process of training can be added to the experience pool, and the updated experience pool can be used to further train the reinforcement learning model. In the process of training the reinforcement learning model, the action (a) in the formed quadruple can be initiated by the DQN and can act on the environment. In the medical field, for example, the action in this case may also include but is not limited to: starting a dialog, ending a dialog, requesting symptom information, diagnosing a disease, etc.

Optionally, in the first example of the present disclosure, when training the reinforcement learning model, external knowledge such as a knowledge graph may be introduced additionally to assist decision-making. In this case, the training results of the reinforcement learning model and the content of the knowledge graph can be considered simultaneously, in order to make the final decision and achieve the purpose of further improving the training effect of the reinforcement learning model.

Second Example

Figure 7:
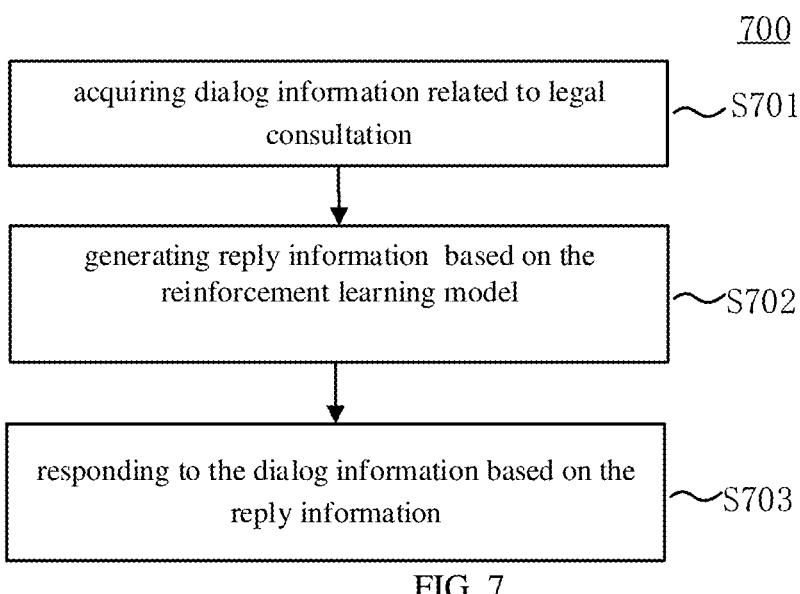
FIG. 7 illustrates an exemplary flowchart of a dialog processing method used in the legal consulting field according to some embodiments of the present disclosure.

In the second example of the embodiments of the present disclosure, an exemplary flowchart of a dialog processing method 700 used in the field of legal consultation is provided, as illustrated in FIG. 7.

In step S701, dialog information related to legal consultation is acquired.

In this step, the acquired dialog information related to legal consultation may be, for example, natural language text related to the legal consultation. Optionally, the dialog information can be understood based on the natural language text, and effective dialog information to be processed can be extracted from the natural language text.

In step S702, reply information is generated based on the reinforcement learning model.

In this step, according to the acquired dialog information related to legal consultation, the reply information that needs to be fed back can be generated based on the reinforcement learning model of DQN. The reinforcement learning model can be obtained by training according to the following method for training a reinforcement learning model:

First, legal clause data (as the labeled data) and legal consultation dialog data (as the unlabeled data) for training the reinforcement learning model can be acquired. In this step, the acquired data used for training the reinforcement learning model may include the legal clause data acquired from electronic legal clauses, and the target information as the user goal can be further extracted from the legal clause data, for example, the target information may include various information such as names of legal clauses, behavior types, behavior performance. Correspondingly, the legal consultation dialog data may be, for example, legal consultation dialog data obtained from the Internet, and the training information of the legal consultation dialog data extracted from the data may include various information such as dialog time, dialog objects, dialog content, application results of legal clauses, etc., which can be saved in the form of, for example, a json file.

Subsequently, based on the legal consultation dialog data, the legal clause data may be served as target information to generate an experience pool for training the reinforcement learning model. For example, it is also possible to first extract effective training information based on the legal consultation dialog data, use the target information extracted from the legal clause data as the training target, and generate the experience pool through interaction with the environment (the user simulator). The experience pool may include one or more quadruples <s, a, r, s'> or <s, a, c'r, s'> including the credibility c', which is not repeated here.

Finally, the experience pool may be used to train the reinforcement learning model. For example, the DQN and the user simulator can be used to interact. During the interaction, the quadruple contained in the experience pool assists in training, and the target information (the user goal) serves as the training target, so as to update parameters in DQN through continuous simulation and iteration, thereby obtaining the final training results.

In step S703, a response is made to the dialog information based on the reply information.

In this step, the generated reply information may be converted into natural language and output, so as to respond to the dialog information.

Figure 8:
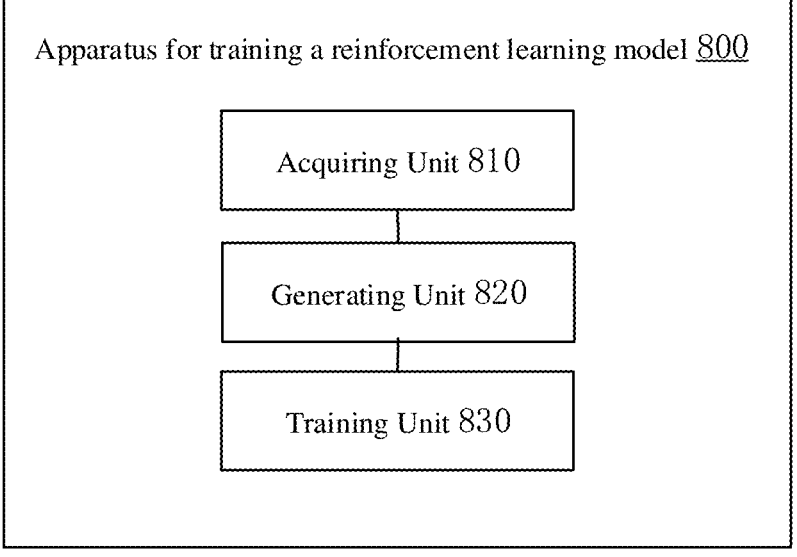
FIG. 8 illustrates a block diagram of a training apparatus for a reinforcement learning model according to some embodiments of the present disclosure.

Hereinafter, an apparatus for training a reinforcement learning model according to the embodiments of the present disclosure is described with reference to FIG. 8. FIG. 8 illustrates a block diagram of an apparatus 800 for training a reinforcement learning model according to some embodiments of the present disclosure. As illustrated in FIG. 8, the apparatus 800 for training the reinforcement learning model includes an acquiring unit 810, a generating unit 820, and a training unit 830. In addition to these units, the apparatus 800 for training the reinforcement learning model may also include other components. However, because these components have nothing to do with the content of the embodiments of the present disclosure, the illustration and description thereof are omitted here. In addition, because the specific details of the following operations performed by the apparatus 800 for training the reinforcement learning model according to the embodiments of the present disclosure are the same as those described above with reference to FIG. 1, the repeated description of the same details is omitted here for avoiding repetition.

The acquiring unit 810 of the apparatus 800 for training the reinforcement learning model in FIG. 8 acquires unlabeled data and labeled data for training the reinforcement learning model.

The data used for training the reinforcement learning model acquired by the acquiring unit 810 includes labeled data. Optionally, the labeled data may be the data obtained from a database related to the field of the reinforcement learning model to be trained. In one example, the training information related to the reinforcement learning model can be extracted from the labeled data, and the extracted training information can be save as, for example, target information of the user (also known as the user goal). The extracted target information from the labeled data can be used for direct training of the reinforcement learning model so as to provide feedback to the agent and to guide the training process. Optionally, the target information extracted from the labeled data may include information corresponding to a result (result), a classification tag (tag), etc., respectively.

Further, the data used for training the reinforcement learning model acquired by the acquiring unit 810 may also include unlabeled data. Optionally, the unlabeled data may be obtained through various manners, and these manners may include unlabeled web pages, forums, chat records, databases and others related to the field of the reinforcement learning model to be trained. Optionally, the unlabeled data may be dialog data. In one example, it is also possible to extract the training information related to the reinforcement learning model from the unlabeled data, and use the extracted training information to subsequently generate an experience pool for training the reinforcement learning model.

Optionally, in the case where the apparatus of the embodiments of the present disclosure is applied in the medical field, the labeled data may be medical case data obtained from, for example, electronic medical records, and the extracted target information may include various information such as diseases, symptom classifications, symptom attributes, and other information. Correspondingly, the unlabeled data may be, for example, medical dialog data obtained from the Internet, and the extracted training information of the unlabeled data may include various information such as dialog time, dialog objects, dialog content, and diagnostic results. Of course, the above content is only for example. In the embodiments of the present disclosure, the apparatus can also be applied to various other fields such as education, legal consultation, shopping and dining inquiries, flight inquiries, navigation, etc., which is not limited here.

The generating unit 820 generates an experience pool for training the reinforcement learning model with reference to the labeled data based on the unlabeled data.

Optionally, the generating unit 820 may generate the experience pool based on the effective training information extracted from the unlabeled data, with the target information extracted from the labeled data being as the training target. Optionally, the experience pool may include one or more sequences consisting of a first state (s), an action (a), a reward score (r), and a second state (s'), and may be represented as a quadruple <s, a, r, s'>. In one example, the action and the first state which is current can be obtained based on unlabeled data, and the second state and the reward score can be obtained through interaction with the environment. In the case where the unlabeled data is dialog data, the action may be any dialog action acquired based on the dialog data, the first state may include all historical information in the dialog data which is before the acquired dialog action, and the historical information may be composed of all the information and actions before the dialog action. Correspondingly, the second state may be the state that the environment migrates to after the action is applied in the case where the environment is in the first state, and the reward score may include the feedback made under the guidance of the labeled data which serves as the target information after the action is applied in the case the environment is in the first state.

Optionally, the reward score in the quadruple used for constructing the experience pool may further include the credibility (c or c') of the action. In other words, in the case where the field of the reinforcement learning model to be trained is known, based on the action (a), the corresponding occurrence probability and specificity thereof in the key information set of the field can be calculated, so as to obtain the credibility (c) of the action, and the processed credibility (c') is obtained after smoothing and normalization processing on the credibility (c). Subsequently, the experience pool can be constructed according to the quadruple <s, a, c'r, s'>.

Optionally, in the case where the apparatus of the embodiments of the present disclosure is applied to the medical field, the generating unit 820 can acquire the action and the first state that is current based on medical dialog data, and acquire the second state and the reward score through the interaction with the environment. The action may be any dialog action acquired based on the medical dialog data. For example, the action includes but is not limited to: starting a dialog, ending a dialog, requesting symptom information, diagnosing a disease, etc., the first state may include all historical information in the medical dialog data which is before the acquired dialog action, and the historical information may be composed of all the information and actions before the dialog action. Correspondingly, the second state may be the state that the environment migrates to after the action is applied in the case where the environment is in the first state; and the reward score may include the feedback made under the guidance of the medical case data which serves as the target information, after the action is applied in the case the environment is in the first state. Optionally, in this case, the credibility of the action included in the reward score can be calculated by the formulas (1)-(3) mentioned above.

Where D={$D^i$} may be a set of diseases, and the set of diseases can include, for example, several diseases encoded by ICD-10. For example, $D^i$ may represent the $i^{th}$ disease (i is 0 or a positive integer), and each disease $D^i$ may include several pieces of medical dialog data. For example, $$d_j^i$$

may represent the $j^{th}$ dialog data for disease $D^i$ (j is 0 or a positive integer), then AF may represent the probability that action (a) appears in the medical dialog data $$d_j^i,$$

IDF represents the specificity that action (a) appears in a specific disease. Therefore, the credibility AF-IDF can be obtained by the product of AF and IDF both, so as to reflect the credibility (c) of a certain action (a). After the credibility (c) is calculated, the processed credibility (c') is obtained after smoothing and normalization processing on the credibility (c), so as to avoid affecting the training results because of some uncollected diseases. Finally, the quadruple <s, a, c'r, s'> can be formed according to the calculated c' so as to construct the experience pool.

The training unit 830 trains the reinforcement learning model by using the experience pool.

In the embodiments of the present disclosure, after the experience pool is generated according to the unlabeled data and the labeled data, the training unit 830 can use the experience pool to assist in training the reinforcement learning model. Optionally, the agent (for example, DQN neural network) and the environment (for example, may be the user simulator) can interact. During the interaction, the quadruple (<s, a, r, s'> or <s, a, c'r, s'>) contained in the experience pool is used to assist in training, and the labeled data or the target information extracted from the labeled data serves as the training target, so as to update parameters in DQN through continuous simulation and iteration, thereby obtaining the final training results. Optionally, in the process of training, the experience pool may be continuously updated by using the quadruple obtained in the process of training, that is, the training unit 830 may add the new quadruple obtained in the process of training to the experience pool, and use the updated experience pool to train the reinforcement learning model. In the process of training the reinforcement learning model, the action (a) in the formed quadruple can be initiated by the DQN and can act on the environment, instead of being obtained from the unlabeled data. In the medical field, for example, the action in this case may also include but is not limited to: starting a dialog, ending a dialog, requesting symptom information, diagnosing a disease, etc.

Optionally, in the embodiments of the present disclosure, the training unit 830 may also introduce additionally external knowledge to assist decision-making when training the reinforcement learning model. In this case, the training results of the reinforcement learning model and the content of the external knowledge can be considered simultaneously, in order to make the final decision and achieve the purpose of further improving the training effect of the reinforcement learning model. In one example, the external knowledge herein may be a database related to the reinforcement learning model, such as a knowledge graph, etc.

In the embodiments of the present disclosure, optionally, the apparatus for training the reinforcement learning model may be used to train a reinforcement learning model for a dialog system. According to different task types of the dialog system, the dialog system may be classified as a task-oriented dialog system and a non-task-oriented dialog system. The task-oriented dialog system refers to a type of dialog system that aims to help users complete tasks in a specific field based on communication with users. In one example, the apparatus for training the reinforcement learning model can be used to train a reinforcement learning model for a task-oriented dialog system, for example, can be used to train a reinforcement learning model for a medical dialog system. Of course, the above content is only for example. In the embodiments of the present disclosure, the apparatus can also be applied to dialog systems related to various other fields such as education, legal consultation, shopping and dining inquiries, flight inquiries, navigation, etc., which is not limited here.

According to the apparatus for training a reinforcement learning model in the embodiments of the present disclosure, the reinforcement learning model can be jointly trained based on unlabeled data and labeled data, thereby effectively reducing the requirements for the labeled data during the training of the reinforcement learning model, improving the feasibility and stability of the training of the reinforcement learning model, and improving the training results of the reinforcement learning model.

Figure 9:
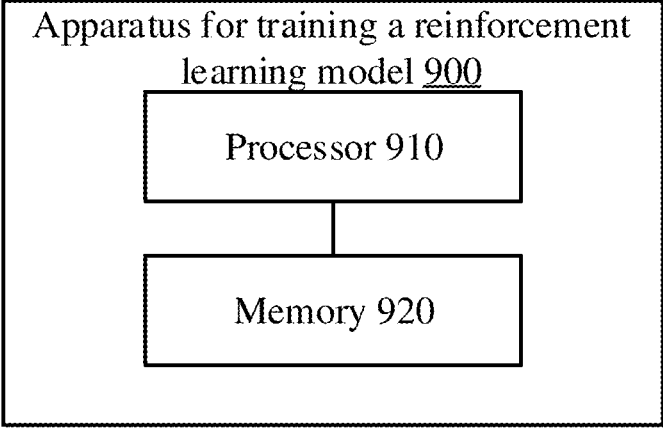
FIG. 9 illustrates a block diagram of a training apparatus for a reinforcement learning model according to some embodiments of the present disclosure.

Hereinafter, an apparatus 900 for training a reinforcement learning model according to the embodiments of the present disclosure is described with reference to FIG. 9. FIG. 9 illustrates a block diagram of an apparatus 900 for training a reinforcement learning model according to some embodiments of the present disclosure. As illustrated in FIG. 9, the apparatus 900 may be a computer or a server.

As illustrated in FIG. 9, the apparatus 900 for training a reinforcement learning model includes one or more processors 910 and a memory 920. Of course, in addition, the apparatus 900 for training the reinforcement learning model may also include an input apparatus and an output apparatus, and others (not shown), these components may be interconnected through a bus system and/or other forms of connection mechanisms. It should be noted that the components and structures of the apparatus 900 for training the reinforcement learning model illustrated in FIG. 9 are only exemplary and not restrictive. According to the requirements, the apparatus 900 for training the reinforcement learning model may also have other components and structures.

The processor 910 may be a central processing unit (CPU) or a field programmable logic array (FPGA) or a single chip microcomputer (MCU) or a digital signal processor (DSP) or an application specific integrated circuit (ASIC), and other logic computing devices having data processing capability and/or program execution capability.

The processor 910 may utilize computer program instructions stored in the memory 920 to perform desired functions, which may include: acquiring unlabeled data and labeled data for training the reinforcement learning model, generating an experience pool for training the reinforcement learning model with reference to the labeled data based on the unlabeled data, and training the reinforcement learning model by using the experience pool.

The computer program instructions include one or more processor operations defined by an instruction set architecture corresponding to the processor, and these computer instructions may be logically contained and represented by one or more computer programs.

The memory 920 may include one or more computer program products, and the computer program products may include various forms of computer-readable storage media, such as volatile memory and/or nonvolatile memory, for example, static random access memory (SRAM), electrically erasable programmable read-only memory (EE-PROM), erasable programmable read-only memory (EPROM), programmable read-only memory (PROM), read-only memory (ROM), magnetic memory, flash memory, magnetic disk or optical disk. One or more computer program instructions can be stored on the computer-readable storage medium, and the processor 910 can execute the program instructions to implement the functions of the apparatus for training the reinforcement learning model of the embodiments of the present disclosure described above and/or other desired functions, and/or implement the method for training the reinforcement learning model according to the embodiments of the present disclosure. Various application programs and various data can also be stored in the computer-readable storage medium.

Hereinafter, a computer-readable storage medium having computer program instructions stored thereon according to the embodiments of the present disclosure is described, and when the computer program instructions are executed by a processor, the following operations are implemented: acquiring unlabeled data and labeled data for training the reinforcement learning model, generating an experience pool for training the reinforcement learning model with reference to the labeled data based on the unlabeled data, and training the reinforcement learning model by using the experience pool.

Figure 10:
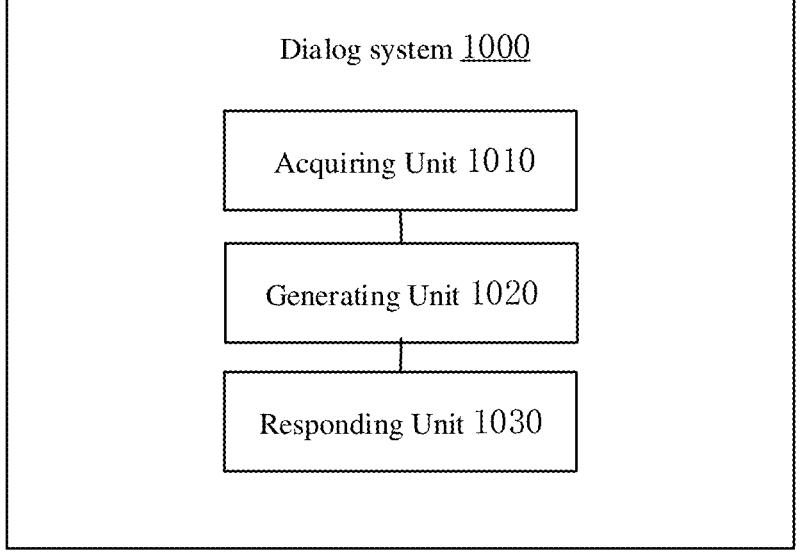
FIG. 10 illustrates a block diagram of a dialog system according to some embodiments of the present disclosure.

Hereinafter, a dialog system according to the embodiments of the present disclosure is described with reference to FIG. 10. FIG. 10 illustrates a block diagram of a dialog system 1000 according to some embodiments of the present disclosure. As illustrated in FIG. 10, the dialog system 1000 includes an acquiring unit 1010, a generating unit 1020, and a responding unit 1030. In addition to these units, the dialog system 1000 may also include other components. However, because these components have nothing to do with the content of the embodiments of the present disclosure, their illustration and description are omitted here. In addition, because the specific details of the following operations performed by the dialog system 1000 according to the embodiments of the present disclosure are the same as those described above with reference to FIG. 2 and FIG. 3, the repeated description of the same details is omitted here for avoiding repetition. In addition, the dialog system 1000 illustrated in FIG. 10 can also be known as a chat information system, spoken dialog system, conversation agent, chatter robot, chatterbot, chatbot, chat agent, digital personal assistant, and automated online assistant, etc. The dialog system 1000 can use natural language to interact with people so as to simulate intelligent conversations and provide personalized assistance to users. The dialog system can be implemented based on a reinforcement learning model. Optionally, the reinforcement learning model on which the system illustrated in FIG. 10 is based can be applied to many fields such as education, legal consultation, shopping and dining inquiries, flight inquiries, navigation and so on.

The acquiring unit 1010 of the dialog system 1000 in FIG. 10 acquires dialog information.

The dialog information acquired by the acquiring unit 1010 may be, for example, natural language text. Optionally, it can be understood based on the natural language text, and the effective dialog information to be processed can be extracted from the natural language text through various operations such as word segmentation, semantic analysis, etc., for use in subsequent dialog processing procedures.

The generating unit 1020 generates reply information based on the reinforcement learning model.

The generating unit 1020 may generate the reply information that needs to be fed back according to the acquired dialog information, based on a reinforcement learning model such as DQN. For example, the reinforcement learning model may be obtained by training through the above-mentioned method or apparatus for training a reinforcement learning model.

The process of training the reinforcement learning model using the above-mentioned method for training a reinforcement learning model is illustrated in FIG. 3. FIG. 3 illustrates an exemplary flowchart of a method for training a reinforcement learning model used in a dialog system according to some embodiments of the present disclosure. Optionally, the reinforcement learning model involved in FIG. 3 can be applied to many fields such as education, legal consultation, shopping and dining inquiries, flight inquiries, navigation and so on.

In step S2021, unlabeled data and labeled data for training the reinforcement learning model are acquired.

In this step, the acquired data used for training the reinforcement learning model includes labeled data. Optionally, the labeled data may be data obtained from a database related to the field of the reinforcement learning model to be trained. In one example, training information related to the reinforcement learning model may be extracted from the labeled data, and the extracted training information may be saved as, for example, target information of the user (also known as the user goal). The extracted target information from the labeled data can be used for direct training of the reinforcement learning model so as to provide feedback to the agent and to guide the training process. Optionally, the target information extracted from the labeled data may include information corresponding to a result (result), a classification tag (tag), etc., respectively.

Further, the acquired data used for training the reinforcement learning model may also include unlabeled data. Optionally, the unlabeled data may be obtained through various manners, and these manners may include unlabeled web pages, forums, chat records, databases, and others related to the field of the reinforcement learning model to be trained. Optionally, the unlabeled data may be dialog data. In one example, it is also possible to extract the training information related to the reinforcement learning model from unlabeled data, and use the extracted training information to subsequently generate an experience pool for training the reinforcement learning model.

Optionally, in the case where the method of the embodiments of the present disclosure is applied to the medical field, the labeled data may be medical case data obtained from, for example, electronic medical records, and the extracted target information may include various information such as diseases, symptom classifications, and symptom attributes. Correspondingly, the unlabeled data may be, for example, medical dialog data obtained from the Internet, and the extracted training information of the unlabeled data may include various information such as dialog time, dialog objects, dialog content, and diagnostic results. Of course, the above content is only for example. In the embodiments of the present disclosure, the method for training can also be applied to various other fields such as education, legal consultation, shopping and dining inquiries, flight inquiries, navigation, etc., which is not limited here.

In step S2022, an experience pool for training the reinforcement learning model is generated with reference to the labeled data based on the unlabeled data.

In this step, optionally, the experience pool may be generated, with the target information extracted from the labeled data being as the training target, based on the effective training information extracted from the unlabeled data. Optionally, the experience pool may include one or more sequences consisting of a first state (s), an action (a), a reward score (r), and a second state (s'), and may be represented as a quadruple $<s, a, r, s'>$. In one example, the action and the first state which is current can be obtained based on unlabeled data, and the second state and the reward score can be obtained through interaction with the environment. In the case where the unlabeled data is dialog data, the action may be any dialog action acquired based on the dialog data, the first state may include all historical information in the dialog data which is before the acquired dialog action, and the historical information may be composed of all the information and actions before the dialog action. Correspondingly, the second state may be the state that the environment migrates to after the action is applied in the case where the environment is in the first state, and the reward score may include the feedback made under the guidance of the labeled data which serves as the target information after the action is applied in the case the environment is in the first state.

Optionally, the reward score in the quadruple used for constructing the experience pool may further include the credibility (c or c') of the action. In other words, in the case where the field of the reinforcement learning model to be trained is known, based on the action (a), the corresponding occurrence probability and specificity thereof in the key information set of the field can be calculated, so as to obtain the credibility (c) of the action, and the processed credibility (c') is obtained after smoothing and normalization processing on the credibility (c). Subsequently, the experience pool can be constructed according to the quadruple $<s, a, c'r, s'>$.

Optionally, in the case where the method of the embodiments of the present disclosure is applied to the medical field, the action and the first state that is current may be acquired based on medical dialog data, and the second state and the reward score may be acquired through the interaction with the environment. The action may be any dialog action acquired based on the medical dialog data. For example, the action includes but is not limited to: starting a dialog, ending a dialog, requesting symptom information, diagnosing a disease, etc., the first state may include all historical information in the medical dialog data which is before the acquired dialog action, and the historical information may be composed of all the information and actions before the dialog action. Correspondingly, the second state may be the state that the environment migrates to after the action is applied in the case where the environment is in the first state; and the reward score may include the feedback made under the guidance of the medical case data which serves as the target information, after the action is applied in the case the environment is in the first state. Optionally, in this case, the credibility of the action included in the reward score can be calculated by the formulas (1)-(3) mentioned above.

Where $D=\{D^i\}$ may be a set of diseases, and the set of diseases can include, for example, several diseases encoded by ICD-10. For example, $D^i$ may represent the $i^{th}$ disease (i is 0 or a positive integer), and each disease $D^i$ may include several pieces of medical dialog data. For example, $$d^i_j$$

may represent the $j^{th}$ dialog data for disease $D^i$ (j is 0 or a positive integer), then AF may represent the probability that action (a) appears in the medical dialog data $$d^i_j,$$

IDF represents the specificity that action (a) appears in a specific disease. Therefore, the credibility AF-IDF can be obtained by the product of AF and IDF, so as to reflect the credibility (c) of a certain action (a). After the credibility (c) is calculated, the processed credibility (c') is obtained after smoothing and normalization processing on the credibility (c), so as to avoid affecting the training results because of some uncollected diseases. Finally, the quadruple <s, a, c'r, s'> can be formed according to the calculated c' so as to construct the experience pool.

In step S2023, the experience pool is used to train the reinforcement learning model.

In the embodiments of the present disclosure, after the experience pool is formed according to unlabeled data and labeled data, the experience pool may be used to assist in training the reinforcement learning model. Optionally, the agent (for example, DQN neural network) and the environment (for example, may be a user simulator) can interact. During the interaction, the quadruple (<s, a, r, s'> or <s, a, c'r, s'>) included in the experience pool is used to assist in training, and the labeled data or the target information extracted from the labeled data serves as the training target, so as to update parameters in DQN through continuous simulation and iteration, thereby obtaining the final training results. Optionally, in the process of training, the experience pool may be continuously updated by using the quadruple obtained in the process of training, that is, the new quadruple obtained in the process of training can be added to the experience pool. Therefore, using the experience pool to train the reinforcement learning model may further include: in the process of training the reinforcement learning model, updating the experience pool according to the training results, and using the experience pool that is updated to train the reinforcement learning model. In the process of training the reinforcement learning model, the action (a) in the formed quadruple can be initiated by the DQN and can act on the environment. In the medical field, for example, the action in this case may also include but is not limited to: starting a dialog, ending a dialog, requesting symptom information, diagnosing a disease, etc.

Optionally, in the embodiments of the present disclosure, when training the reinforcement learning model, external knowledge may be introduced additionally to assist decision-making. In this case, the training results of the reinforcement learning model and the content of the external knowledge can be considered simultaneously, in order to make the final decision and achieve the purpose of further improving the training effect of the reinforcement learning model. In one example, the external knowledge herein may be a database related to the reinforcement learning model, such as a knowledge graph, etc.

Returning to FIG. 10, the responding unit 1030 responds to the dialog information based on the reply information.

The responding unit 1030 may convert the generated reply information into natural language and output it so as to respond to the dialog information.

According to the dialog system of the embodiments of the present disclosure, the reinforcement learning model can be jointly trained based on unlabeled data and labeled data, thereby effectively reducing the requirements for the labeled data during the training of the reinforcement learning model, improving the feasibility and stability of the training of the reinforcement learning model, and improving the training results of the reinforcement learning model.

Figure 11:
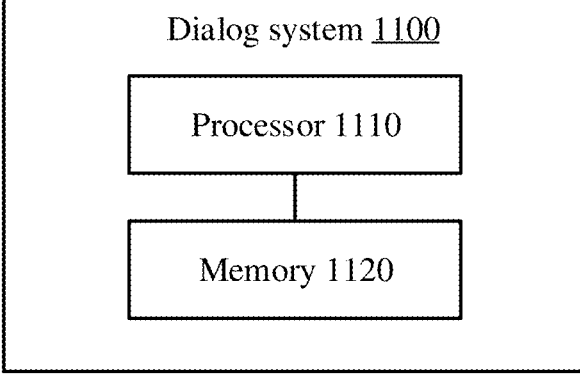
FIG. 11 illustrates a block diagram of a dialog system according to some embodiments of the present disclosure.

Hereinafter, a dialog system 1100 according to some embodiments of the present disclosure is described with reference to FIG. 11. FIG. 11 illustrates a block diagram of a dialog system 1100 according to some embodiments of the present disclosure. As illustrated in FIG. 11, the apparatus 1100 may be a computer or a server.

As illustrated in FIG. 11, the dialog system 1100 includes one or more processors 1110 and a memory 1120. Of course, in addition to these components, the dialog system 1100 may also include an input apparatus, an output apparatus (not shown), etc. The components can be interconnected through a bus system and/or other forms of connection mechanisms. It should be noted that the components and structures of the dialog system 1100 illustrated in FIG. 11 are only exemplary and not restrictive, and the dialog system 1100 may also include other components and structures as required.

The processor 1110 may be a central processing unit (CPU), a field programmable logic array (FPGA), a single chip microcomputer (MCU), a digital signal processor (DSP), or an application specific integrated circuit (ASIC), and other logic computing devices having data processing capability and/or program execution capability, and can use the computer program instructions stored in the memory 1120 to perform desired functions, which may include: acquiring dialog information; generating reply information based on a reinforcement learning model; and responding to the dialog information based on the reply information. For example, the reinforcement learning model is trained by: acquiring unlabeled data and labeled data for training the reinforcement learning model; generating an experience pool for training the reinforcement learning model with reference to the labeled data based on the unlabeled data; and training the reinforcement learning model by using the experience pool.

The memory 1120 may include one or more computer program products, and the computer program products may include various forms of computer-readable storage media, such as volatile memory and/or nonvolatile memory, for example, static random access memory (SRAM), electrically erasable programmable read-only memory (EEPROM), erasable programmable read-only memory (EPROM), programmable read-only memory (PROM), read-only memory (ROM), magnetic memory, flash memory, magnetic disk or optical disk. One or more computer program instructions can be stored on the computer-readable storage medium, and the processor 1110 can execute the program instructions to implement the functions of the apparatus for training the reinforcement learning model of the embodiments of the present disclosure described above and/or other desired functions, and/or implement the dialog processing method according to the embodiments of the present disclosure. Various application programs and various data can also be stored in the computer-readable storage medium.

Hereinafter, a computer-readable storage medium having computer program instructions stored thereon according to the embodiments of the present disclosure is described, and when the computer program instructions are executed by a processor, the following operations are implemented: acquiring dialog information; generating reply information based on a reinforcement learning model; and responding to the dialog information based on the reply information. For example, the reinforcement learning model is trained by: acquiring unlabeled data and labeled data for training the reinforcement learning model; generating an experience pool for training the reinforcement learning model with reference to the labeled data based on the unlabeled data; and training the reinforcement learning model by using the experience pool.

As described above, the dialog system of the embodiments of the present disclosure is particularly applicable to the medical field. Relative to other fields, the labeled data in the medical field is very little, because the requirements for labeling data are relatively high, that is, doctors having higher professionalism and experience are required to label data, so as to improve the professionalism and accuracy. By adopting the method for training the reinforcement learning model of the present disclosure, the reinforcement learning model can be jointly trained based on the unlabeled data and the labeled data, thereby reducing the dependence and requirements on the professionalism and experience of doctors, and effectively reducing the requirements for the labeled data during the training of the reinforcement learning model.

Figure 12:
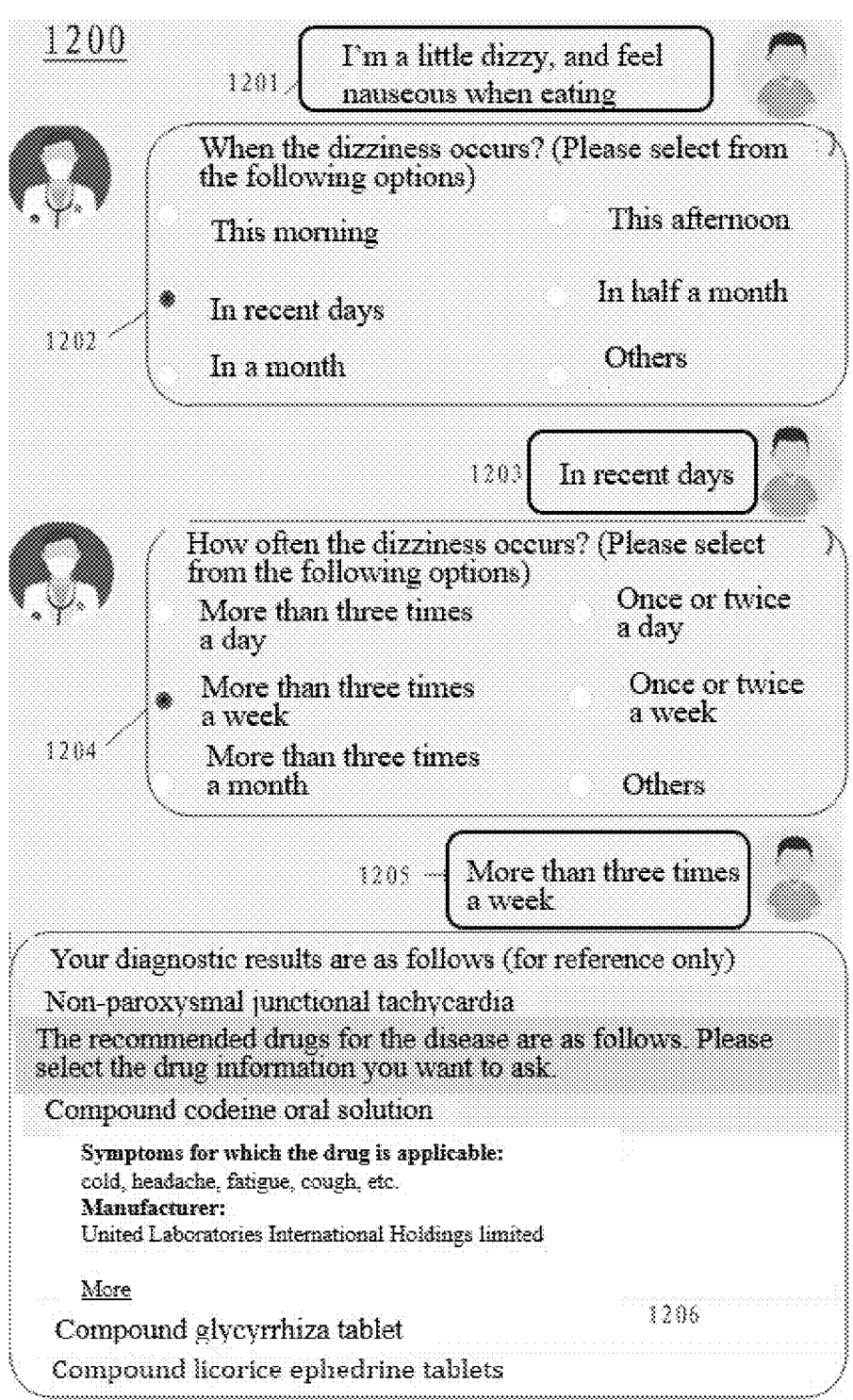
FIG. 12 illustrates a schematic diagram of a user interface 1200 of a medical dialog system according to some embodiments of the present disclosure.

FIG. 12 illustrates a schematic diagram of a user interface 1200 of a medical dialog system according to some embodiments of the present disclosure.

Optionally, the model involved in the medical dialog system can be obtained by training using the method for training the reinforcement learning model described above. The model can be stored in the form of a computer program instruction set. The medical dialog system may include: a user interface, a processor, and a memory having computer program instructions stored thereon, and when the computer program instructions are executed by the processor, the processor is caused to perform the following operations.

As illustrated in FIG. 12, the medical dialog system first receives natural language input information from a user, and the natural language input information is displayed on the user interface 1200 (for example, on the right side). The natural language input information can be input by voice or text. For example, as illustrated in block 1201, the user uses text to input the natural language input information of "I am a little dizzy, and feel nauseous when eating."

Optionally, the medical dialog system performs the named entity recognition process on the natural language input information so as to extract symptom information. For example, the medical dialog system extracts "dizzy" and/or "nauseous" symptom information from the natural language input information of "I am a little dizzy, and feel nauseous when eating". The following uses "dizzy" as an example.

Then, the medical dialog system displays one or more questions associated with the symptoms mentioned in the natural language input information on the user interface 1200 (for example, on the left side), so as to implement multiple rounds of questions and answers, and for each question, an answer to the question is received from the user, and the answer is displayed on the right side of the user interface.

Specifically, after extracting the symptom information "dizzy", the medical dialog system displays a question asking when the dizziness occurs on the user interface (below the block 1201 and on the left side) (block 1202). The question can be provided together with multiple answer options in which the user can choose. The user gives an answer to the question and the answer is displayed on the right side of the user interface (below the block 1202). For example, when the user answers the question (block 1202) and selects the option "in recent days", the text "in recent days" would be displayed in block 1203. Then, the next round of question and answer can be performed. The medical dialog system displays a question about the frequency of dizziness (block 1204) on the user interface (below the block 1203 and on the left side). Similarly, the question can be provided together with multiple answer options in which the user can choose. The user gives an answer to the question and the answer is displayed on the user interface (below block 1204 and on the right side). For example, when the user answers the question (1204) and selects the option "more than three times a week," then the text "more than three times a week" is displayed in block 1205. The multiple rounds of questions and answers are completed in similar manners. Although only two rounds of questions and answers are illustrated in FIG. 12, there may be more rounds of questions according to the method for training the reinforcement learning model of the medical dialog system, which is not limited in the present disclosure.

Finally, after multiple rounds of questions and answers, the medical dialog system generates and displays the diagnostic results for the symptoms on the user interface, as illustrated in block 1206.

Optionally, the diagnostic results include at least one of: possible disease types, symptoms of the possible disease types, recommended drugs applicable for the possible disease types, symptoms targeted by the recommended drugs, and links to learn more about the recommended drugs, etc.

Optionally, the diagnostic results may also include the probability of various disease types to which the symptoms may correspond.

Optionally, the diagnostic results are output and displayed on the user interface in the form of natural language, for example, as illustrated in block 1206.

In the above embodiments, for ease of understanding and description, the functional units corresponding to the functions to be performed are described. It is easy to understand that these functional units are functional entities and do not necessarily correspond to entities which are physically or logically independent. These functional entities can be implemented by a general-purpose processor running software corresponding to the functions in the form of executing computer instructions, or these functional entities can be implemented programmatically in one or more hardware modules or integrated circuits, or these functional entities can be implemented by integrated circuits designed to specifically perform corresponding functions.

For example, the general-purpose processor may be a central processing unit (CPU), a single-chip microcomputer (MCU), a digital signal processor (DSP), or the like.

For example, the programmable integrated circuit may be a field programmable logic circuit (FPGA).

For example, the specialized integrated circuit may be an application specific integrated circuit (ASIC), such as a tensor processing unit (TPU).

The program part in the technology can be regarded as a "product" or "article" which exists in the form of executable code and/or related data, which is participated in or implemented by a computer-readable medium. The tangible and permanent storage medium may include any memory or storage used by computers, processors, or similar devices or related modules. For example, various semiconductor memories, tape drives, disk drives, or similar devices that can provide storage functions for software.

All software or part of it may sometimes communicate through a network, such as the Internet or other communication networks. This type of communication can load software from one computer device or processor to another, for example, from a server or host computer of an image retrieval device to a hardware platform of computer environment, or other computer environments that implement the system, or a system having similar functions related to providing information required for image retrieval. Therefore, another medium that can transmit software elements can also be used as a physical connection between local devices, such as light waves, electric waves, electromagnetic waves, and the communication is implemented through cables, optical cables, or air. The physical media used for carrier waves, such as cables, wireless connections, or optical cables, can also be considered as media that carry software. Unless limited to the tangible "storage" medium, other terms representing the computer or machine "readable medium" represent the medium that participates in the process of executing any instructions by the processor.

The present disclosure uses specific words to describe the embodiments of the present disclosure. For example, "first/second embodiment", "one embodiment", and/or "some embodiments" indicate a certain feature, structure, or characteristic related to at least one embodiment of the present disclosure. Therefore, it should be emphasized and noted that "an embodiment" or "one embodiment" or "an alternative embodiment" mentioned twice or more in different positions in this specification does not necessarily indicate a same embodiment. In addition, certain features, structures, or characteristics in one or more embodiments of the present disclosure can be appropriately combined.

In addition, those skilled in the art can understand that various aspects of the present disclosure can be illustrated and described through several patentable categories or situations, including any new and useful process, machine, product or combination of substances, or any new and useful improvements to them. Correspondingly, various aspects of the present disclosure can be completely executed by hardware, can be completely executed by software (including firmware, resident software, microcode, etc.), or can be executed by a combination of hardware and software. The above hardware or software can be called "data block," "module," "engine," "unit," "component" or "system," In addition, various aspects of the present disclosure may be embodied as a computer product located in one or more computer-readable media, and the product includes computer-readable program code.

Unless otherwise defined, all terms (including technical and scientific terms) used herein have the same meaning as commonly understood by those of ordinary skill in the art to which the present disclosure belongs. It should also be understood that terms such as those defined in ordinary dictionaries should be interpreted as having meanings consistent with their meanings in the context of related technologies, and should not be interpreted in idealized or extremely formalized meanings, unless explicitly defined herein.

The above is the description of the present disclosure and should not be considered as a limitation thereof. Although several exemplary embodiments of the present disclosure are described, those skilled in the art readily understand that many modifications can be made to the exemplary embodiments without departing from the novel teachings and advantages of the present disclosure. Therefore, all these modifications are intended to be included in the scope of the present disclosure defined by the claims. It should be understood that the above is the explanation of the present disclosure, and should not be considered as being limited to the specific embodiments disclosed, and the modifications to the disclosed embodiments and other embodiments are intended to be included in the scope of the appended claims. The present disclosure is defined by the claims and their equivalents.

What is claimed is:

1. A method for training a reinforcement learning model based on neural networks for a medical dialog system, performed by a processor and comprising:

acquiring unlabeled data and labeled data for training the reinforcement learning model, wherein the unlabeled data is medical dialog data, and/or the labeled data is medical case data;

generating an experience pool for training the reinforcement learning model with reference to the labeled data, based on the unlabeled data, wherein the experience pool includes one or more sequences consisting of a first state(s), an action (a), a reward score (r), and a second state (s'); and training the reinforcement learning model using the experience pool, wherein training comprises:

making the reinforcement learning model and the environment interact using one or more sequences from the experience pool;

generating one or more new sequences during the interaction, wherein each of the one or more of the newly generated sequences include a first state(s), an action (a), a reward score (r), and a second state (s'), the reward score being related to feedback made under guidance of the labeled data and a credibility of the action;

iteratively updating the experience pool by adding the newly generated sequences to the experience pool; and updating parameters of the reinforcement learning model through continuous simulation and iteration using the updated experience pool for subsequent reinforcement learning iterations, thereby obtaining final training results;

wherein target information extracted from the labeled data is used as a training target for training the reinforcement learning model, and wherein the experience pool is generated based on training information extracted from the unlabeled data under the guidance of the target information extracted from the labeled data, and wherein the credibility of the action which is determined based on an occurrence probability and specificity of the action in a key information set in a medical field, and wherein occurrence probability is an occurrence probability of the action in corresponding medical dialog data, and the specificity is a specificity of the action under a specific disease.

2. The method according to claim 1, wherein each sequence in the experience pool represents a state transition, and wherein the second state (s') is a state to which the environment migrates after the action (a) is applied when the environment is in the first state (s).

3. The method according to claim 1, wherein the action is a dialog action acquired from the medical dialog data; and wherein the first state comprise historical information in the medical dialog data which is before the acquired dialog action.

4. A dialog processing method for a medical dialog system, performed by a processor and comprising:

acquiring dialog information;

generating reply information based on a reinforcement learning model based on neural networks; and responding to the dialog information based on the reply information;

wherein the reinforcement learning model is trained through the following operations:

acquiring unlabeled data and labeled data for training the reinforcement learning model, wherein the unlabeled data is medical dialog data, and/or the labeled data is medical case data;

generating an experience pool for training the reinforcement learning model with reference to the labeled data, based on the unlabeled data, wherein the experience pool includes one or more sequences consisting of a first state(s), an action (a), a reward score (r), and a second state (s'); and training the reinforcement learning model using the experience pool, wherein training comprises:

making the reinforcement learning model and the environment interact using one or more sequences from the experience pool;

generating one or more new sequences during the interaction, wherein each of the one or more of the newly generated sequences include a first state(s), an action (a), a reward score (r), and a second state (s'), the reward score being related to feedback made under guidance of the labeled data and a credibility of the action;

iteratively updating the experience pool by adding the newly generated sequences to the experience pool; and updating parameters of the reinforcement learning model through continuous simulation and iteration using the updated experience pool for subsequent reinforcement learning iterations, thereby obtaining final training results;

wherein target information extracted from the labeled data is used as a training target for training the reinforcement learning model, and wherein the experience pool is generated based on training information extracted from the unlabeled data under the guidance of the target information extracted from the labeled data, and wherein the credibility of the action which is determined based on an occurrence probability and specificity of the action in a key information set in a medical field, and wherein occurrence probability is an occurrence probability of the action in corresponding medical dialog data, and the specificity is a specificity of the action under a specific disease.

5. The method according to claim 4, wherein responding to the dialog information based on the reply information comprises:

converting the reply information into natural language and outputting the natural language.

6. A medical dialog system, comprising:

a user interface;

a processor;

a memory, having computer program instructions stored thereon, which when executed by the processor, cause the processor to:

receive natural language input information from a user and display the natural language input information on the user interface;

display one or more questions associated with a symptom mentioned in the natural language input information on the user interface;

for each question, receive an answer responding to a question from the user, and display the answer on the user interface, and generate and display diagnostic results for the symptom on the user interface, after question and answer operation is finished, wherein the medical dialog system is based on a reinforcement learning model based on neural networks trained through the following operations:

acquiring unlabeled data and labeled data for training the reinforcement learning model, wherein the unlabeled data is medical dialog data, and/or the labeled data is medical case data;

generating an experience pool for training the reinforcement learning model with reference to the labeled data, based on the unlabeled data, wherein the experience pool includes one or more sequences consisting of a first state(s), an action (a), a reward score (r), and a second state (s'); and training the reinforcement learning model using the experience pool, wherein training comprises:

making the reinforcement learning model and the environment interact using one or more sequences from the experience pool;

generating one or more new sequences during the interaction, wherein each of the one or more of the newly generated sequences include a first state(s), an action (a), a reward score (r), and a second state (s'), the reward score being related to feedback made under guidance of the labeled data and a credibility of the action;

iteratively updating the experience pool by adding the newly generated sequences to the experience pool; and updating parameters of the reinforcement learning model through continuous simulation and iteration using the updated experience pool for subsequent reinforcement learning iterations, thereby obtaining final training results;

wherein target information extracted from the labeled data is used as a training target for training the reinforcement learning model, and wherein the experience pool is generated based on training information extracted from the unlabeled data under the guidance of the target information extracted from the labeled data, and wherein the credibility of the action which is determined based on an occurrence probability and specificity of the action in a key information set in a medical field, and wherein occurrence probability is an occurrence probability of the action in corresponding medical dialog data, and the specificity is a specificity of the action under a specific disease.

7. The medical dialog system according to claim 6, wherein the diagnostic results comprise at least one of: possible disease types, symptoms of the possible disease types, recommended drugs applicable for the possible disease types, symptoms targeted by the recommended drugs, and links to learn more about the recommended drugs.

8. The medical dialog system according to claim 7, wherein the diagnostic results are output and displayed on the user interface in the form of natural language.

9. The medical dialog system according to claim 6, wherein the question comprises a plurality of options, so that the user selects one of the plurality of options as the answer.

10. The medical dialog system according to claim 6, wherein the instructions further cause the processor to perform a named entity recognition process on the natural language input information so as to extract symptom information.

11. The medical dialog system according to claim 6, wherein the medical dialog system further generates the diagnostic results based on a knowledge graph, the knowledge graph comprises nodes of M diseases and N symptoms, and corresponding relationships between various diseases and various symptoms, where M and N are integers greater than or equal to 1, and the knowledge graph further comprises recommended drugs, preventive measures, treatment schemes, and etiology for each disease.

* * * * *